United States Patent [19]

Bantel et al.

[11] Patent Number: 4,644,162

[45] Date of Patent: Feb. 17, 1987

[54] COOLING HOLE INSPECTION

[75] Inventors: Thomas E. Bantel, Cincinnati, Ohio; David C. Mack, Waukesha, Wis.

[73] Assignee: General Electric Company, Cincinnati, Ohio

[21] Appl. No.: 652,245

[22] Filed: Sep. 20, 1984

[51] Int. Cl.$^4$ ............................................. G01N 21/71
[52] U.S. Cl. .................................... 250/340; 250/334; 374/5
[58] Field of Search ........... 250/330, 334, 340, 338 R; 374/5, 15, 45

[56] References Cited

U.S. PATENT DOCUMENTS 3,566,669 3/1971 Lawrence et al. ...................... 374/5

FOREIGN PATENT DOCUMENTS 2125556 3/1984 United Kingdom .................. 374/45

OTHER PUBLICATIONS

"Infrared Scanner Detects Coating Defects", *Materials Engineering*, Oct. 1983, p. 24.
"Thermal Diffusivity Measures Thin Films", *Lasers & Applications*, May 1984, p. 36.
Document entitled *Tech Update* containing article entitled "British Seek Way to Test Composites".

*Primary Examiner*—Alfred E. Smith
*Assistant Examiner*—Constantine Hannaher
*Attorney, Agent, or Firm*—Gregory A. Welte; Derek P. Lawrence

[57] ABSTRACT

In the present invention, the temperatures of cooling passages in a gas turbine engine blade are changed, as by forcing a heated gas through them. The infrared signatures of the channels are measured during the initial temperature transient of the channels and the signatures are compared with a reference. The reference may be the signature of other channels on the same blade.

3 Claims, 4 Drawing Figures

COOLING HOLE INSPECTION

The Government has rights in this invention pursuant to Contract No. F33615-80-C-5106 awarded by the Department of the Air Force.

The present invention relates to the inspection of holes to determine that they have been properly manufactured and, more specifically, to the inspection of cooling channels in gas turbine engine blades.

BACKGROUND OF THE INVENTION

Gas turbine engine blades contain channels which lead from an exterior surface to an interior plenum. An example is shown in FIG. 1, wherein a blade 2 contains a plenum 3 to which channels 6 connect and lead to an external surface 9. In use, pressurized air is applied to the plenum 3 causing cooling airstreams 12 to flow through the channels 6, thereby absorbing heat from the walls of the channels 6, as well as from the surface 9 of the blade 2, thereby cooling the blade 2.

In order to function properly, the channels 6 must be constructed to a known configuration because the distribution of airflow must be controlled in order to achieve proper cooling. Restated, the channels 6 must not be blocked, not even partially. However, inspection of channels 6 to detect blockages from the external surface 9 is difficult. One reason is that they are very small, a typical diameter being 12 mils (0.3 mm), and thus it is nearly impossible to insert a diameter measurement gage into the channels 6.

OBJECTS OF THE INVENTION

It is an object of the present invention to provide a new and improved inspection apparatus for inspecting channels.

It is a further object of the present invention to provide new and improved inspection system for the inspection of cooling channels in gas turbine engine blades.

SUMMARY OF THE INVENTION

In one form of the present invention, the temperatures of cooling passages in a gas turbine engine blade are changed, as by forcing a heated gas through them. The infrared signatures of the channels are measured during the initial temperature transient of the channels and the signatures are compared with a reference. The reference may be the signature of other channels on the same blade.

DETAILED DESCRIPTION OF THE INVENTION

Figure 2:
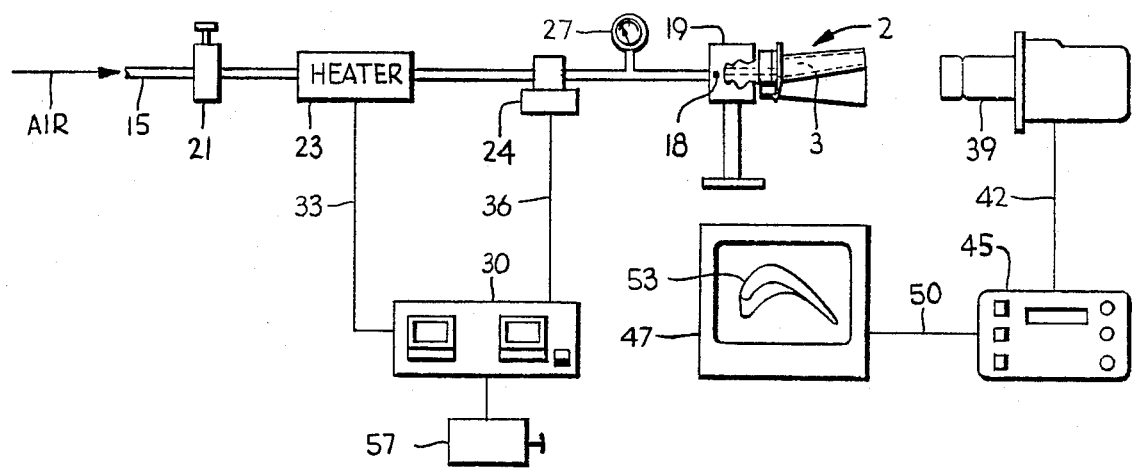
FIG. 2 illustrates one form of the present invention.

FIG. 2 illustrates one form of the present invention, wherein line 15 receives filtered, compressed air and delivers it to point 18 at which the air is fed to the internal plenum 3 contained in the gas turbine engine blade 2. The blade 2 is held by a fixture 19. Interconnected in line 15 is a pressure regulator 21, an air heater 23, a solenoid valve 24, and a pressure gage 27. A computerized control 30, known in the art, controls the air heater 23 and the solenoid valve 24 by respective electrical lines 33 and 36. A scanning infrared radiometer 39, herein called an IR camera, such as Model No. 525, available from inframetrics, located in Bedford, MA., takes an image of the channels 6 through which the heated air provided at point 18 is escaping, and transmits a signal along electrical line 42 to an electronics package 45, available from Inframetrics, whih is associated with Model No. 525, which transmits signals to a video monitor 47 along line 50. This scanning radiometer is responsive to radiation in approximately the 9–12 micron range. A representative image 53 is shown on the monitor.

In operation, an operator will mount the turbine blade in the fixture 19 and activate the control 30 through a switch 57. The control opens the solenoid 24 and activates the heater 23 to admit a heated airstream (not specifically shown) to the plenum 3.

Applicants have found that the heated airstream causes the channels 6, when they are very small (less than 0.035 inches (0.89 mm) in diameter), to act as black body cavity radiators. As such, they approach behaving as idealized sources of radiation in accordance with Planck's well known, empirically ascertained law. Applicants utilize this finding in examining channels 6 for blockages as follows.

Figure 1:
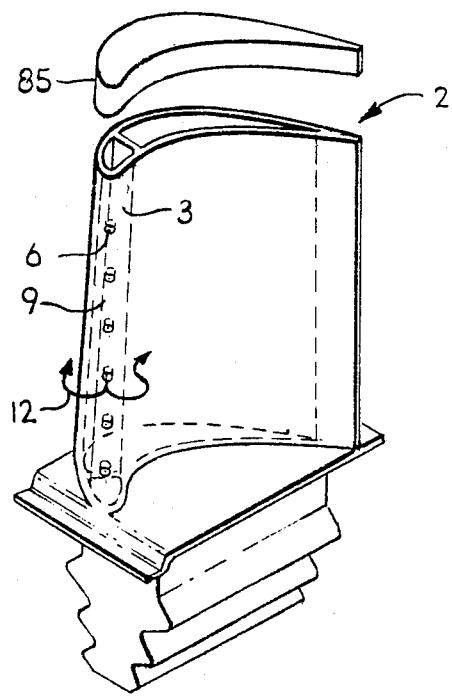
FIG. 1 illustrates a gas turbine engine blade of the type examined by the present invention.
Figure 3:
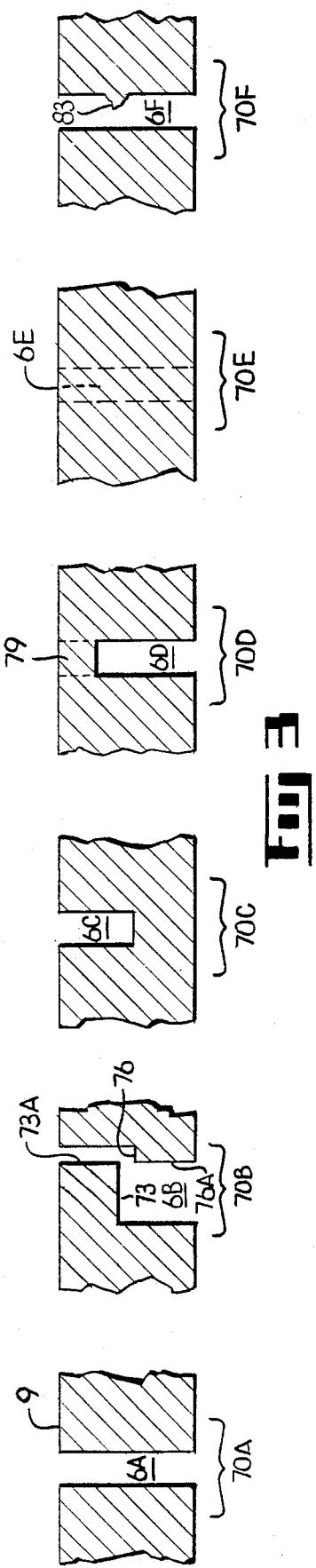
FIG. 3 illustrates six different types of cooling holes and defects which can be contained by the blade in FIG. 1.

Six different types of blockage are shown in FIG. 3 in six different regions 70A–F. Region 70A contains a properly formed channel 6A. Region 70B contains a channel which contains a "jink" caused by two adjacent sharp turns 73 and 76. (Because of details which need not be understood by the reader, walls 73A and 76A tend to be co-linear when a jink is formed.) Region 70C contains an improperly drilled channel 6C which is blocked at its bottom. Region 70D contains a brazed-over channel 6D which is capped by a cap 79 of brazing alloy or blade coating material. The fifth type of blockage is shown in region 70E and it is a blockage in which no channel, not even a partial one, exists. The fully blocked channel is designated 6E for reference. Region 70F contains a partially blocked channel 6F containing a blockage 83. (The situations in the two regions 70D and F can result from mishaps in which brazing alloy accidentally overflows and forms the cap 79 in region 70D, or in which it overflows and forms the blockage 83 in region 70F. Brazing alloy is sometimes used to fasten a tip cap 85 in FIG. 1 to a blade 2. Further, the braze alloy or other coating material itself can sometimes form a cap 79 in region 6D in FIG. 3.) Some of the six blockages have been found to be distinguishable from the others based on their infrared signatures, as detected by the IR camera 39 in FIG. 2.

For example, during the initial transient, immediately following the introduction of hot air (preferably at 200° F. (370 K.) or higher) into the plenum 3 of the blade 2, the channels 6A–E in FIG. 3 radiate with intensities of decreasing magnitude from left to right in the Figure: channel 6A is the brightest and channel 6E is the dimmest. (Channel 6F is not now being considered.) After about two seconds, the three channels 6A, B and C are about equally bright, channel 6D is less bright, and the absent channel 6E in region 70E radiates at the same level as the rest of the background.

Figure 4:
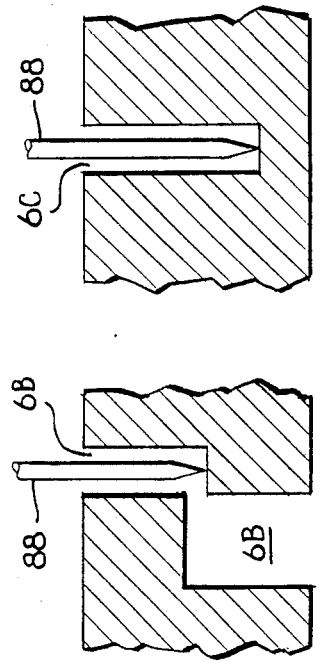
FIG. 4 illustrates a depth measurement of two of the holes in FIG. 3.

Several important pieces of information are available from these differences in brightness. One, during the transient, the blocked channel 6C is distinguishable from the open channel 6A, as is the jinked channel 6B. Two, the capped channel 6D begins to radiate similar to 6A, 6B and 6C following the initial transient because of the emissivity of the brazing material of which the cap 79 is constructed. This similarity allows channel 6D to be distinguished from the absent channel in region 70E. The channel cap radiates more because of its increased temperature. The absent channel and the capped channel 6D could otherwise look similar to a visual observer. Three, the results show that the jinked channel 6B in fact carries cooling air and may be usable as a cooling channel in a blade. An observer examining the jinked channel 6B with a needle probe 88 in FIG. 4 would probably confuse the jinked channel 6B with the blocked channel 6C, in that insertion of the needle probe 88 would be similarly thwarted in both channels. The observer using the needle probe 88 would probably classify the jinked channel 6B as a blocked channel 6C and conclude that the jinked channel 6B carries no cooling air.

Applicants have not been able to obtain blockages 83 in channel 6F as shown in FIG. 3. However, based on Applicants' experience with the rest of the channels in FIG. 3, Applicants theorize that the partially blocked channel 6F will radiate slightly less than the open channel 6A during the transient. Further, the partially blocked channel 6F should radiate almost equally as the open channel 6A following the transient. Thus, the combination of the transient radiance and the steady-state radiance (i.e., radiance less than that of the clear channel 6A at first, followed by radiance greater than that of the jinked channel 6B or the blocked channel 6C), indicates the presence of partial blockage 83.

Although the use of hot air passing through a cold channel has been described, the present invention contemplates the use of cold air passing through a relatively warm channel. The important aspect is that the temperature, and thus the emissivity, of the channels 6A-F in FIG. 3 be rendered different than that of the surface material 9.

An invention has been described wherein obstructions in a channel are ascertained by measuring the infrared signature of the channel when a heated (or cooled) gas, such as air, is forced through it, and, specifically, the infrared signature occurring during the initial transient phase of the air injection. The infrared signatures are compared with each other but, of course, they may be compared with another reference, such as a photograph of previously examined channels.

Numerous substitutions and modifications can be undertaken without departing from the true spirit and scope of the present invention.

What is desired to be secured by Letters Patent is the invention as defined in the following claims.

We claim:

1. A method of inspecting a channel, comprising the following steps:
    (a) causing the temperature of the channel to change;
    (b) measuring the transient of the infrared signature of the channel; and
    (c) comparing the measured transient with a reference.

2. A method of inspecting cooling channels in a gas turbine engine blade, comprising the following steps:
    (a) changing the temperature of the channels by forcing a gas through the channels;
    (b) viewing the channels with a scanning infrared radiometer and generating an image which indicates the relative intensities of black-body radiation emitted by the channels; and
    (c) comparing the intensities of paragraph (b) with each other during the initial temperature transient of the channels.

3. A method of inspecting the cooling holes in a gas turbine engine blade, comprising the steps of:
    (a) changing the temperatures of the holes by passing air through them;
    (b) viewing the holes using a scanning radiometer which is responsive to radiation in approximately the 9–12 micron range;
    (c) deriving at least two images at different times of the holes using the radiometer; and
    (d) comparing the images with reference images.

* * * * *